United States Patent [19]
Protopapas et al.

[11] Patent Number: 5,868,683
[45] Date of Patent: *Feb. 9, 1999

[54] TECHNIQUES FOR PREDICTING READING DEFICIT BASED ON ACOUSTICAL MEASUREMENTS

[75] Inventors: Athanassios Protopapas; Michael M. Merzenich, both of San Francisco, Calif.; Merav Ahissar, Rehovot, Israel

[73] Assignee: Scientific Learning Corporation, Berkeley, Calif.

[*] Notice: This patent issued on a continued prosecution application filed under 37 CFR 1.53(d), and is subject to the twenty year patent term provisions of 35 U.S.C. 154(a)(2).

[21] Appl. No.: 957,680

[22] Filed: Oct. 24, 1997

[51] Int. Cl.$^6$ .................................................. G06F 15/00
[52] U.S. Cl. ........................................ 600/559; 434/116
[58] Field of Search ........................... 600/559; 434/112, 434/113, 114, 116; 435/25; 705/26; 340/825.19

[56] References Cited

U.S. PATENT DOCUMENTS

| | | | |
|---|---|---|---|
| 4,969,096 | 11/1990 | Rosen et al. | 434/112 |
| 5,122,952 | 6/1992 | Minkus | 705/26 |
| 5,260,196 | 11/1993 | Comings | 435/25 |

OTHER PUBLICATIONS

Ludlow et al., "Auditory Processing Skills of Hyperactive, Language–Impaired, and Reading–Disabled Boys", 1983, Central Auditory Processing Disorders, Baltimore: University Park Press, pp. 163–184.

Willy De Weirdt, "Speech Perception and Frequency Discrimination in Good and Poor Readers," 1988, Applied Psycholinguistics, Cambridge University Press, pp. 163–183.

Hari et al. "Deficit of Temporal Auditory Processing in Dyslexic Adults," 1996, Neuroscience Letters 205, Helsinki University of Technology, pp. 138–140.

McCroskey et al., "Auditory Fusion among Learning Disabled, Reading Disabled, and Normal Children," 1980, Journal of Learning Disabilities, vol. 13, No. 2, pp. 19–25.

Watson et al., "Auditory Temporal Processing in Relation to Reading and Math Disabilities," 1993, Annals NY Academy of Sciences, 682, pp. 418–420.

Marjorie A. Reed, "Speech Perception and the Discrimination of Brief Auditroy Cues in Reading Disabled Children," 1989, Journal of Experimental Child Psychology, vol. 48, pp. 270–292.

Dermody et al., "Dichotic Listening in Good and Poor Readers," 1983, Journal of Speech and Hearing Research, vol. 26, American Speech–Language Hearing Association, pp. 341–348.

McNally et al., "Auditory Temporal Coding in Dyslexia," 1996, The Royal Society, pp. 961–965.

Witton et al., "Sensitivity to Dynamic Auditory and Visual Stimuli Predicts Nonword Reading Ability in Both Dyslexic and Normal Readers," 1998, Current Biology, vol. 8, http://biomednet.com/elecref/0960982200800791, pp. 791–797.

(List continued on next page.)

Primary Examiner—George Manuel
Attorney, Agent, or Firm—Beyer & Weaver, LLP

[57] ABSTRACT

A computer-implemented method for predicting, diagnosing and/or treating reading deficit in a human being is disclosed. The method includes generating a set of tonal stimuli, which includes at least a first tonal stimulus and a second tonal stimulus. The first tonal stimulus is separated from the second tonal stimulus by an interval. The computer-implemented method further includes providing the set of tonal stimuli to the human being and receiving a response from the human being. The response from the human being indicates a perception by the human being pertaining to the set of tonal stimuli. Further, the computer-implemented method includes ascertaining a first parameter pertaining to the set of tonal stimuli at which the response is inaccurate. The first parameter is one of a frequency parameter and a time parameter. The first parameter indicates that the human is susceptible to the reading deficit if the first parameter is above a predefined parameter value.

16 Claims, 5 Drawing Sheets

OTHER PUBLICATIONS

Tallal et al., "Perceptual/Motor Profiles of Reading Impaired Children With or Without Concomitant Oral Languaage Deficits," 1982, Annals of Dyslexia, vol. 32, pp. 163–177.

Paula Tallal, "Auditory Temporal Perception, Phonics, and Reading Disabilities in Children," 1980, University of California at San Diego and Children's Hospital of San Diego, Brain and Language vol. 9, pp. . 182–198.

Woodcock et al., "Tests of Cognitive Ability Test Record," ©1989 by The Riverside Publishing Company, pp. 1–32.

Woodcock et al., "Tests of Cognitive Ability Supplemental Battery," ©1989 by The Riverside Publishing Company, pp. 1–497.

Woodcock et al., "Tests of Cognitive Ability Standard Battery," ©1989 by The Riverside Publishing Company, pp. 1–331.

Richard W. Woodcock, "Woodcock Reading Mastery Tests–Revised NU Test Record G," ©1998, American Guidance Service, Inc., pp. 1–16.

Richard W. Woodcock, "Woodcock Reading Mastery Test–Revised NU Test Record H," ©1998, American Guidance Service, Inc., pp. 1–12.

Richard W. Woodcock, "Woodcock Reading Mastery Tests–Revised Forms G and H Examiners Manual," ©1987, 1998, American Guidance Service, Inc., pp. ii–202.

"GORT–3 Gray Oral Reading Tests Profile/Examiner Record Booklet Form A 3rd Ed.," ©1992. 1986, 1967 by PRO–ED, Inc.

"GORT–3 Gray Oral Reading Tests Profile/Examiner Record Booklet Form B 3rd Ed.," ©1992. 1986, 1967 by PRO–ED, Inc.

Wiederholt et al., GORT–3 Gray Oral Reading Tests Student Book Forms A and B 3rd Ed., ©1992, 1986, 1967 by PRO–ED, Inc.

Wiederholt et al., Gray Oral Reading Tests Examiner's Manual, 3rd ed., ©1992, 1986, 1967 by PRO–ED, Inc., pp. iii–65.

Woodcock et al., "Tests of Cognitive Ability Standard and Supplemental Batteries Norm Tables," ©1989 DLM Teaching Resources, pp. iii–294.

Gary S. Wilkinson, WRAT3 Wide Range Achievement Test Revision 3, Blue Test Scores, ©1993 by Jastak Associates A Division of Wide Range, Inc., pp. 1–4.

Gary S. Wilkinson, WRAT3 Wide Range Achievement Test Revision 3, Tan Test Scores, ©1993 by Jastak Associates A Division of Wide Range, Inc., pp. 1–4.

Gary S. Wilkinson, WRAT3 Wide Range Achievement Test Administration Mannual, 1993 Edition, ©1993 by Wide Range, Inc.

Richard W. Woodcock, "Woodcock Reading Mastery Tests–Revised Form H Test Book," ©1987 American Guidance Service, Inc.

Richard W. Woodcock, "Woodcock Reading Mastery Tests–Revised Form G. Test Book," ©1987 American Guidance Service, Inc.

TECHNIQUES FOR PREDICTING READING DEFICIT BASED ON ACOUSTICAL MEASUREMENTS

BACKGROUND OF THE INVENTION

The present invention relates generally to techniques for improving learning in people. More particularly, the present invention relates to improved techniques for diagnosing, predicting, and treating reading deficit in a person based on acoustical measurements.

Reading deficit (RD) is an impairment in the ability of a person to read, decode, and comprehend written words. Such an impairment often presents a serious obstacle to social and/or economic success. This is because deficiencies in reading skills, in addition to causing difficulties in comprehending written words and in learning, may lead to low self-esteem and/or a host of other learning-related social problems.

Fortunately, reading deficit often admits remediation although success rates of the various available method may vary considerably. If a person is identified as having a reading deficit, his reading skills may be improved using a variety of intervention techniques known in the art, such as training and/or therapy. Indeed, if susceptibility to reading deficit is detected sufficiently early, young children may, for example, be given supplemental training and/or therapy to strengthen the skills required for successful reading even before they reach their reading age. In this manner, these young children may undergo intervention programs early on and acquire sufficient skills to at least keep up with their peers by the time they start learning to read, thereby minimizing learning-related self-esteem and/or other related social problems.

In the prior art, there exists a variety of techniques for identifying whether a particular person suffers from reading deficit. However, these prior art techniques typically focus on formulating reading tests that can accurately ascertain whether a particular person is deficient in reading skills. For example, a person suspected of suffering from reading deficit may, according to one prior art technique, be asked to read one or more written passages from a standardized reading test. A comparison of the accuracy and/or reading rate of the test subject to the accuracy and/or reading rate of those deemed to be normal readers may then suggest whether that test subject may have reading deficit symptoms.

To screen individuals (children) before school age (and thus before reading instruction), there exist in the prior art a testing technique based on language skills called "phonological awareness," which is broadly defined as the ability to consciously break words into their constituent sounds (phonemes), to combine phonemes in order to form words, and to recognize certain speech-sound regularities such as rhyming. The ability to perform the aforementioned tasks has been shown to be related to current as well as future reading ability (with respect to age-appropriate levels).

Another test, termed "rapid naming," consists in the verbal report of the identity of a number of drawings of familiar objects and animals. The number of drawings that can be named in a predefined time interval (e.g., one minute) is believed to relate to the facility with which reading will likely be initiated. Other tests, such as memory, posture balance, attention, etc., have been employed to screen preschool children for possible future reading problems.

Although such prior art techniques may, if properly designed and administered, be able to identify with a fair degree of accuracy those suffering from reading deficit, there are disadvantages. By way of example, the use of a reading test requires that the test subject be at least of reading age, i.e., old enough to read the written passages, and that the tests be normed separately for each language (to determine the expected performance levels of a normal reader). Accordingly, such reading tests are inapplicable for use in predicting reading deficit in pre-reading children, i.e., children who are too young to read, and they are also inapplicable for use with individuals of other linguistic backgrounds than the one the test is made in.

With respect to screening tests that do not require any degree of reading competence, such as the aforementioned language skills based tests, they disadvantageously require the constant supervision of a trained adult throughout the duration of test, because a human is required to administer and score every test component. Of course, the human supervisor must be competent in a child's (or adult test subject's) native language in order for the test results to be valid. Additionally, they require, as mentioned earlier, separately developing and norming the test battery for each possible target language, because language-based tests such as those of phonological awareness and rapid naming will have different items and different responses in each language.

In view of the foregoing, there are desired improved techniques for identifying, in a reliable manner, whether a particular person is likely to suffer from reading deficit. The improved reading deficit identifying techniques preferably employ testing methodologies that are capable of identifying reading deficit or the increased probability that such an impairment will develop even in test subjects who are of pre-reading age or who are non-native.

SUMMARY OF THE INVENTION

The invention relates, in one embodiment, to a computer-implemented method for predicting, diagnosing and/or treating reading deficit in a human being. The computer-implemented method includes generating a set of tonal stimuli, which includes at least a first tonal stimulus and a second tonal stimulus. The first tonal stimulus is separated from the second tonal stimulus by an interval. The computer-implemented method further includes providing the set of tonal stimuli to the human being and receiving a response from the human being. The response from the human being indicates a perception by the human being pertaining to the set of tonal stimuli. Further, the computer-implemented method includes ascertaining a first parameter pertaining to the set of tonal stimuli at which the response is inaccurate. The first parameter is one of a frequency parameter and a time parameter. The first parameter indicates that the human is susceptible to the reading deficit if the first parameter is above a predefined parameter value.

In another embodiment, the invention relates to a computer-implemented method for predicting reading deficit in a human being based on acoustic measurements. The method includes generating a first tonal stimulus having a first frequency and generating a second tonal stimulus having a second frequency. The method further includes providing the first tonal stimulus to the human being and providing the second tonal stimulus to the human being. There is further included receiving a response from the human being, the response having at least two response values. A first response value of the two response values indicates a first perception by the human being that the first tonal stimulus equals the second tonal stimulus. The second response value of the two response values indicates a second perception of the human being that the first tonal stimulus differs from the second tonal stimulus. Additionally, the method includes ascertaining a frequency difference at which the response is inaccurate. The frequency difference represents a difference between the first frequency and the second frequency, with the frequency difference indicating the human being susceptible to the reading deficit if the frequency difference is above a predefined value.

These and other features of the present invention will be described in more detail below in the detailed description of the invention and in conjunction with the following figures.

BRIEF DESCRIPTION OF THE DRAWINGS

The present invention is illustrated by way of example, and not by way of limitation, in the figures of the accompanying drawings in which.

DETAILED DESCRIPTION OF THE PREFERRED EMBODIMENTS

The present invention will now be described in detail with reference to a few preferred embodiments thereof as illustrated in the accompanying drawings. In the following description, numerous specific details are set forth in order to provide a thorough understanding of the present invention. It will be apparent, however, to one skilled in the art, that the present invention may be practiced without some or all of these specific details. In other instances, well known process steps and/or structures have not been described in detail in order to not unnecessarily obscure the present invention.

In accordance with one aspect of the present invention, there are provided techniques for identifying RD based on acoustical tests. It has been found that there is a correlation between an individual's performance on certain acoustical tests and his susceptibility to reading deficit. In particular, it has been discovered that RD may be predicted with a reasonable degree of accuracy based on a set of RD-predictive acoustical tests, which employ a plurality of tonal stimuli having varying frequencies, varying inter-stimulus interval (ISI), and/or varying auditory masks. By using acoustical tests based on basic tonal stimuli, the complexities of prior art testing techniques are advantageously avoided. Due to the simplicity of the inventive RD prediction technique, it indeed becomes possible to employ the inventive RD-predictive acoustical tests to predict RD even in children below the reading age or in non-native speakers.

While not wishing to be bound by theory, it is believed that a deficit in auditory processing in the speech frequency range, i.e., about 100 Hz to about 6000 Hz leads to a deficit in language learning. It is believed that when a person, whether a child or an adult, fails to process sounds at an acceptable rate, resolution (e.g., inter-stimulus interval or ISI) and with sufficient clarity (e.g., with accurate perception of the frequency of a sound's components), that person may encounter difficulties in mapping a particular spoken sound to a speech sound in his mind. In other words, if the sound heard cannot be resolved reasonably unambiguously into a particular speech sound in the mind of the child early on in life, that child may have difficulty processing the words being spoken.

If the auditory processing deficit is not particularly severe, redundancy in spoken language may permit the child to compensate as he grows up (e.g., by resolving ambiguous words using context) and may permit the grown child to be able to process spoken language. On the other hand, if the auditory processing deficit is particularly severe, the child may not be able to compensate for the auditory processing deficit and a language learning deficit typically results. Irrespective of whether a language learning deficit results, the auditory processing deficit generally makes it difficult for the child to map a sound heard with a letter or a group of letters normally representative of that sound. By way of example, if the child is confused as to whether a sound heard represents a "b" or a "d," these two letters may be represented by the same sound in the child's mind. Over time, the confusion typically leads to a reading deficit.

From this understanding, it has been theorized that since auditory perception affects reading ability over time, it may be possible to assess or predict reading deficit using tests based on auditory perception. It is also theorized that improvement in auditory perception through training may remedy reading deficit. This aspect of the present invention is particularly important since it involves clinical applications of acoustical measurements to assess, predict, or treat RD.

Further, since speech sounds are generally limited to a fairly narrow frequency range, it is further theorized that the auditory test employed may be based on sounds whose frequencies are generally limited to the frequency range of speech sounds. Still further, although reading deficit is being predicted through the auditory tests, it is advantageously realized that the auditory tests may be based on simple tonal sounds that are understandable even to children of pre-reading age. For example, even simple monotone, non-phoneme sounds within the frequency range of speech may be used to test for RD. By limiting the auditory tests to tonal stimuli within a narrow frequency range, the auditory test may be substantially simplified and made more accurate for the prediction of reading deficit than language-based tests.

With the present invention, it is possible to assess in advance whether a child may need intervention early on, e.g., supplemental reading and language training, so that the child may keep up with his peers during the subsequent schooling years. With supplemental training, the child may also avoid being labeled and/or treated by his teacher, parents, and/or peers as a slow reader or a slow learner, thereby reducing the potential for developing reading-related self-esteem and/or other related social problems.

Further, tonal sounds are universal and are not limited to any particular language. In a highly advantageous manner, the use of simple tonal sounds in the inventive RD-predictive auditory tests may also permit testing to be performed on any test subject irrespective of his or her native language. Also, the use of simple tonal sounds in RD predictive auditory tests substantially simplifies the test such that education or training does not affect their predictive values; i.e., these variables are substantially eliminated in the prediction/assessment of whether a given individual suffers from or is likely to suffer reading deficit.

In accordance with another aspect of the present invention, the RD-predictive acoustical tests may be employed to remedy or treat reading deficit. Once a test subject is found to suffer from or is likely to suffer from reading deficit, the RD-predictive acoustical tests may be administered repeatedly to sharpen the auditory processing skills. In this manner, these "tests" are now employed as remediation training tools. It is believed that an improvement in auditory processing skills tends to lead to improvement in language and/or reading skills.

In accordance with another aspect of the present invention, the RD-predictive acoustical test includes a frequency discrimination test in which the test subject is presented in a sequential manner with a pair of tonal stimuli. The pair of tonal stimuli, which have frequencies within the speech frequency range, are separated from each other by a time interval and also by a given separation frequency. The test subject is then asked to respond whether they perceive the pair of tonal stimuli to have the same or different frequencies. The frequencies of the pair of tonal stimuli are then randomized with the separation frequencies progressively reduced in subsequent pairs of tonal stimuli administered. By recording the minimum separation frequency at which the test subject could no longer discriminate between tonal stimuli having different frequencies and comparing that minimum separation frequency with a predefined value, it has been found that reasonably accurate prediction may be made with regard to that tester's susceptibility to RD.

In accordance with still another aspect of the present invention, the RD-predictive acoustical test includes a frequency salience test in which the test subject is also presented with a pair of tonal stimuli that are separated from each other by a given time interval. The pair of tonal stimuli generally have frequencies within the speech frequency range. Each tone further has associated with it an auditory mask, i.e., a masking sound, which is administered sometime after the tone itself is administered but before the next tone. The test subject is then asked to respond whether they perceive the pair of tonal stimuli to have the same or different frequencies. The frequencies of the pair of tonal stimuli are then randomized with the time separation between an auditory mask and its associated tonal stimulus progressively reduced in subsequent pairs of tonal stimuli administered. By recording the minimum time separation, i.e., the minimum time separating an auditory mask and its associated tonal stimulus, at which the test subject could no longer discriminate between tonal stimuli having different frequencies and comparing that minimum time separation with a predefined time separation value, it has been found that reasonably accurate prediction may also be made with regard to that tester's susceptibility to RD.

In accordance with yet another aspect of the present invention, the RD-predictive acoustical test includes a repetition test in which the test subject is presented in a sequential manner with a plurality of tonal stimuli. The tonal stimuli, which have frequencies within the speech frequency range, are separated from one another by a given inter-stimulus interval (ISI), with each tonal stimulus having a fixed frequency. The test subject is then asked to identify the tones by their relative frequencies. By way of example, a two-tone repetition test may yield, depending on the frequencies of the tonal stimuli, answers of high/low, low/high, low/low, high/high. The inter-stimulus interval between the tonal stimuli is then progressively reduced in subsequent pairs of tonal stimuli administered. By recording the minimum inter-stimulus interval at which the test subject could no longer accurately identify the tones, it has been found that reasonably accurate prediction may also be made with regard to that tester's susceptibility to RD.

In accordance with still another aspect of the present invention, the RD-predictive acoustical test includes any combination of the aforementioned frequency discrimination test, frequency salience test, and repetition test. By employing multiple tests to predict RD, it has been found that RD prediction may be made more accurate for some individuals than can be made by any single one of the above tests.

In accordance with yet another aspect of the present invention, the inventive RD-predictive acoustical testing techniques are optimized for fully computerized testing. By way of example, the nonverbal and simple nature of the stimuli of the inventive RD-predictive acoustical tests makes it possible for a wide variety of computers, including relatively simple computer terminals, to generate the required stimuli for testing. Additionally, the responses from the test subjects are designed such that they do not require any intervention or supervision by another trained human being to administer, interpret and/or score the tests. As long as the appropriate instructions are provided, which may be prerecorded in the appropriate language and/or level of sophistication suitable for the test subjects, the entire testing can be performed by the test subject using a computer without involving any other person. In this manner, testing can be done with a high degree of convenience at a relatively low cost.

Figure 1:
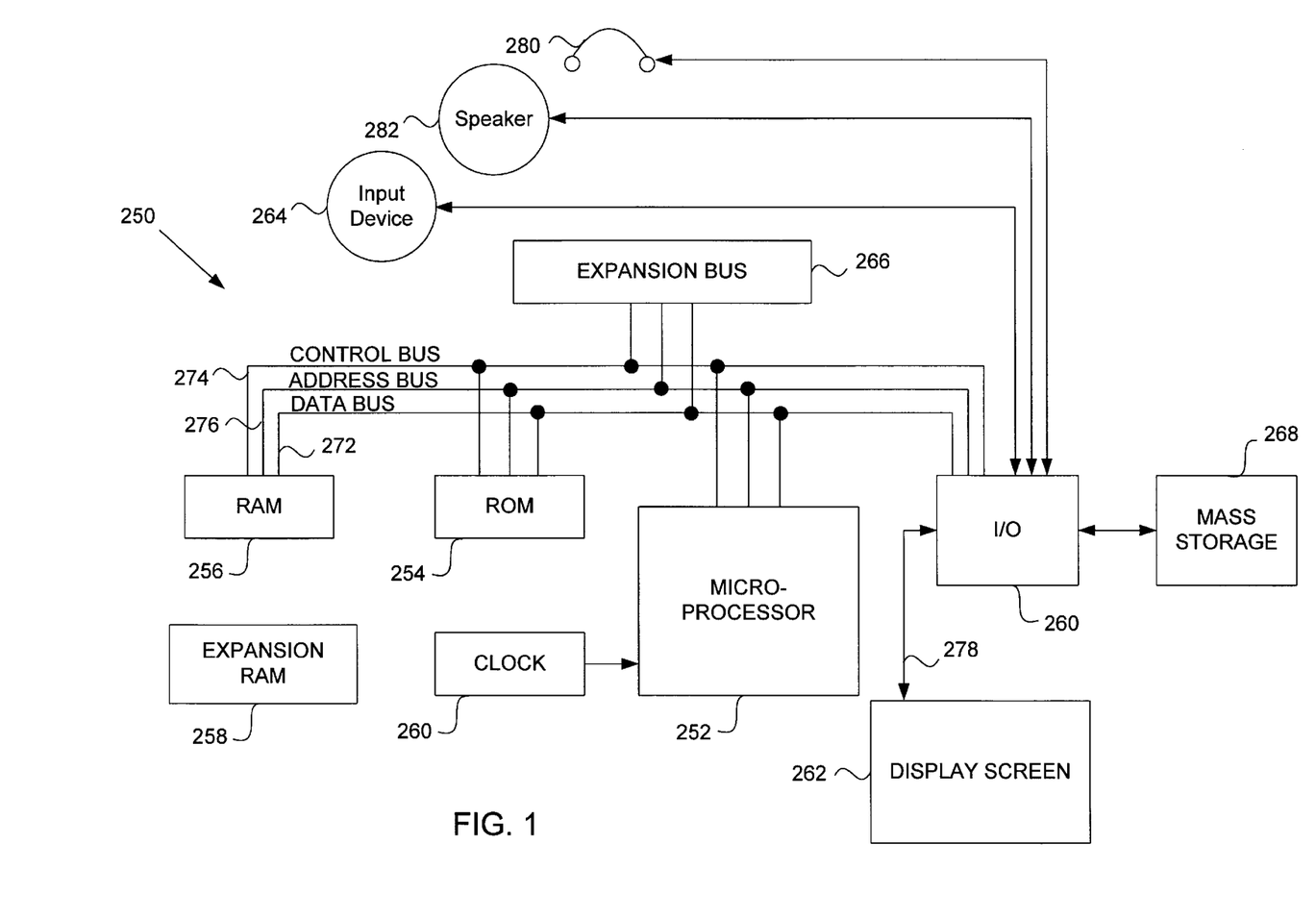
FIG. 1 shows a general purpose computer system, representing a computer suitable for implementing the present inventive RD prediction method.

In general, the RD-predictive acoustical tests may be generated and administered using computer-implemented techniques. FIG. 1 shows a general purpose computer system, representing a computer suitable for implementing the present inventive RD prediction method. Referring to FIG. 1, a computer system 250 in accordance with the present invention includes a central processing unit (CPU) 252, read only memory (ROM) 254, random access memory (RAM) 256, expansion RAM 258, input/output (I/O) circuitry 260, display assembly 262, input device 264, and expansion bus 266. Computer system 250 may also optionally include a mass storage unit 268 such as a disk drive unit or nonvolatile memory such as flash memory and a real-time clock 260. In one embodiment, mass storage unit 268 may include units which utilizes removable computer readable media, such as floppy disks, opto-magnetic media, optical media, and the like for the storage of programs and data.

CPU 252 is preferably a commercially available, single chip microprocessor such as one of the Intel X86 or Motorola 680XX family of chips, a reduced instruction set computer (RISC) chip such as the PowerPC™ microprocessor available from Motorola, Inc, or any other suitable processor. CPU 252 is coupled to ROM 254 by a data bus 272, control bus 274, and address bus 276. ROM 254 may partially contain the basic operating system for the computer system 250. CPU 252 is also connected to RAM 256 by busses 272, 274, and 276 to permit the use of RAM 256 as scratch pad memory. Expansion RAM 258 is optionally coupled to RAM 256 for use by CPU 252. CPU 252 is also coupled to the I/O circuitry 260 by data bus 272, control bus 274, and address bus 276 to permit data transfers with peripheral devices.

I/O circuitry 260 typically includes a number of latches, registers and direct memory access (DMA) controllers. The purpose of I/O circuitry 260 is to provide an interface between CPU 252 and such peripheral devices as display assembly 262, input device 264, mass storage 268, headphone 280, speaker 282, and/or any other I/O device. Display assembly 262 of computer system 250 is an output device for displaying objects and other visual representations of data.

The screen for display assembly 262 can be a device that uses a cathode-ray tube (CRT), liquid crystal display (LCD), or the like, of the types commercially available from a variety of manufacturers. Input device 264 can be a keyboard, a mouse, a stylus working in cooperation with a position-sensing display, or the like. Alternatively, input device 264 can be an embedded RF digitizer activated by an "active" RF stylus. As a further alternative, input device 264 may be any type of switches capable of communicating a user response to computer system 250. Therefore, as used herein, the term input device will refer to any mechanism or device for entering data and/or pointing to a particular location on a screen of a computer display. The aforementioned input devices are available from a variety of vendors and are well known in the art.

Some type of mass storage 268 is generally considered desirable. However, mass storage 268 can be eliminated by providing a sufficient amount of RAM 256 and expansion RAM 258 to store user application programs and data. In that case, RAMs 256 and 258 can optionally be provided with a backup battery to prevent the loss of data even when computer system 250 is turned off. However, it is generally desirable to have some type of long term mass storage 268 such as a commercially available hard disk drive, nonvolatile memory such as flash memory, battery backed RAM, PC-data cards, or the like.

The acoustical signals generated by computer system 250 may be output to the tester using either headphone 280 or speaker 282. In general headphone 280 and speaker 282 may represent any suitable transducer device for generating sound waves responsive to signals from computer system 250.

In operation, computer system 250 is employed to generate tonal stimuli of the various tests. These tonal stimuli may be furnished to the test subject using either headphone 280 or speaker 282. Responses from the user may then be recorded by input device 264 and analyzed by CPU 252 to predict or ascertain RD. If desired, feedback to the user may be given at various stages of the test(s) via display assembly 262.

It should be borne in mind that although computer system 250 is discussed in detail herein to facilitate discussion, the inventive RD prediction technique may be practiced on a variety of suitable computer-implemented technique. By way of example, the inventive RD prediction technique disclosed herein may be implemented via a computer network, such as a local area network (LAN), wide area network (WAN) or a global computer network such as the Internet. In the latter case, the inventive RD prediction technique may be implemented as downloadable computer software and data (e.g., applets). The downloadable computer software and data may be kept on one or more servers on the network, accessible by any client computer or terminal capable and authorized for such access. To facilitate testing, the downloadable computer software and data can be downloaded once and reused over and over at the client computer/terminal. Alternatively, the downloadable computer software and data can be downloaded for each individual testing session via the network as needed. Network computing techniques and implementations therefor are well known in the art and are not discussed in great detail here for brevity's sake.

Frequency Discrimination

Figure 2:
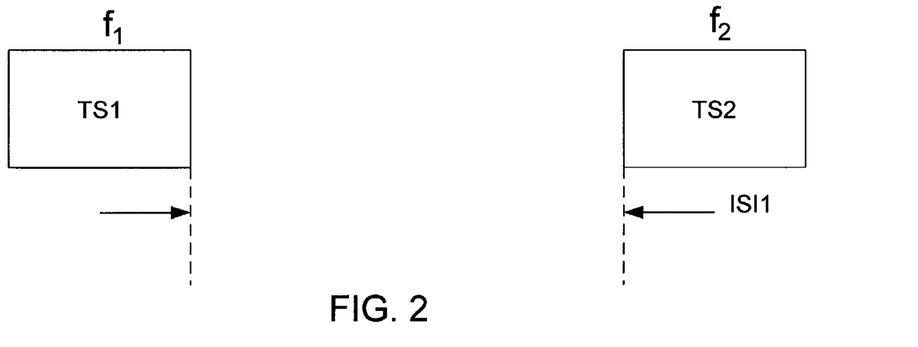
FIG. 2 illustrates, in accordance with one embodiment of the present invention, exemplary tonal stimuli TS1 and TS2, which are administered to the test subject as a sequential pair of tonal stimuli to test for frequency discrimination.

FIG. 2 illustrates, in accordance with one embodiment of the present invention, exemplary tonal stimuli TS1 and TS2, which are administered to the test subject as a sequential pair of tonal stimuli to test for frequency discrimination. Each of tonal stimuli TS1 and TS2 preferably has a sufficiently long duration such that duration is not a significant variable in the frequency discrimination test. In one example, a tone duration of about 250 milliseconds works well for tonal stimulus TS1 and/or tonal stimulus TS2. However, a tone duration may range from between about 10 milliseconds and about 1000 milliseconds.

As shown in FIG. 2, tonal stimulus TS1 is separated from tonal stimulus TS2 by an inter-stimulus interval ISI1, which is again preferably sufficiently long such that the inter-stimulus interval does not become a significant variable in the frequency discrimination test. An inter-stimulus interval ISI1 of about 800 milliseconds works well in one example. However, the inter-stimulus interval may range from between about 0 milliseconds and about 2000 milliseconds. To substantially eliminate loudness (amplitude) as a significant variable, tonal stimuli TS1 and TS2 preferably have the same amplitude. In general, any amplitude within the range of hearing comfort may be employed, e.g., about 70 dB SPL (Sound Pressure Level) in one example.

To test for frequency discrimination, the frequency of tonal stimulus TS1 and/or tonal stimulus TS2 is permitted to change such that their separation frequency (i.e., their frequency difference) is progressively reduced in subsequent tonal stimuli pairs. Preferably, the frequency f1 of tonal stimulus TS1 and/or f2 of tonal stimulus TS2 is kept within the speech frequency range (i.e., between about 100 Hz and about 5000 Hz). In one example, the frequencies f1 and f2 of respective tonal stimuli TS1 and TS2 are randomized within the range of about 600 Hz to about 1400 Hz, with their separation frequencies gradually approach zero as the test progresses.

For each tonal stimuli pair, the test subject is asked to listen to the first tonal stimulus and then the second tonal stimulus in sequence. These tonal stimuli may be generated by the aforementioned computer system using its software and/or hardware and administered to the test subject via an appropriate transducer such as the speaker or headphone. Thereafter, the test subject is asked to identify whether the two tonal stimuli are the same or different. Alternatively, the test subject may be asked to identify which of the two tonal stimuli has the higher frequency. The response may be input into the computer system using the aforementioned input device, e.g., a mouse, keyboard, or the like.

At some frequency separation, the test subject's answer will become inaccurate, i.e., the test subject will no longer be able to discriminate between the frequencies of the tonal stimuli. When this happens, the test may be discontinued or may be permitted to continue for some time with the frequency separation centered around the point at which frequency discrimination previously failed in order to eliminate freak errors. By way of example, an adaptive staircase procedure may be employed wherein the frequency separation is progressively reduced until frequency discrimination failure occurs. After frequency discrimination failure occurs, the frequency separation may be arbitrarily enlarged and then progressively reduced again to validate the failure frequency. This sequence may occur many times if desired.

It has been found that people with RD tend to require a much larger frequency separation for reliable frequency discrimination. The minimum frequency separation value for a given test depends, in part, on other parameters of the test, e.g., duration of each tone, amplitude of each tone, ISI, the structure of the test sequence. In one example, a frequency separation of about 100 Hz or more may be needed for reliable frequency discrimination by people with RD, versus about 50 Hz or less (e.g., about 10–30 Hz) for normal people. In some cases, RD prediction accuracy approaches 80% using the frequency discrimination test alone, i.e., the test can be employed to predict RD accurately 80% of the time.

Figure 3:
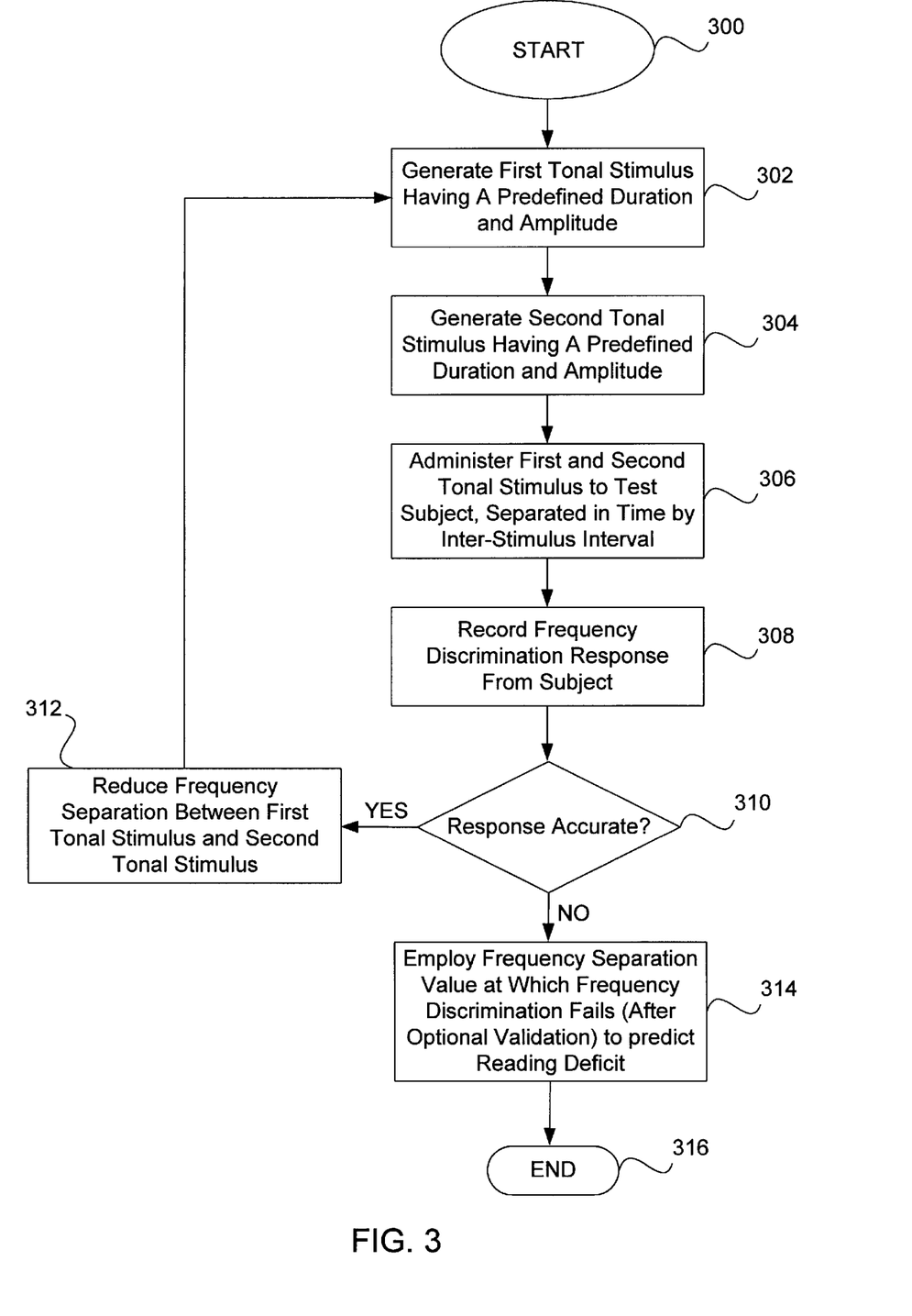
FIG. 3 illustrates, in accordance with one aspect of the present invention, the computer-implemented technique for generating the tonal stimuli employed for RD prediction based on frequency discrimination.

FIG. 3 illustrates, in accordance with one aspect of the present invention, the computer-implemented technique for generating the tonal stimuli employed for RD prediction based on frequency discrimination. In step 302, the first tonal stimulus is generated. The duration and amplitude of this first tonal stimulus are preferably set at predefined values in order to eliminate their influence on the frequency discrimination test result. In step 304, the second tonal stimulus is generated. Again, the duration and amplitude of this first tonal stimulus is preferably set at predefined values in order to eliminate their influence on the frequency discrimination test result. In step 306, the first and second tonal stimuli are administered to the test subject. However, it may be possible, in one embodiment, to administer each tonal stimulus after it is generated independent of the other tonal stimulus. In step 308, the response from the test subject is recorded. If the response is accurate (step 310), the frequency separation value between the first tonal stimulus and the second tonal stimulus is reduced (step 312), and the method returns to step 302 to generate another tonal stimuli pair. On the other hand, if the response is inaccurate (as determined in step 310), the frequency separation value at which frequency discrimination fails is employed to predict RD (step 314). As also indicated in step 314, additional validation steps (e.g., the aforementioned adaptive staircase procedure) may be employed to ensure the accuracy of the test.

Frequency Salience

Figure 4:
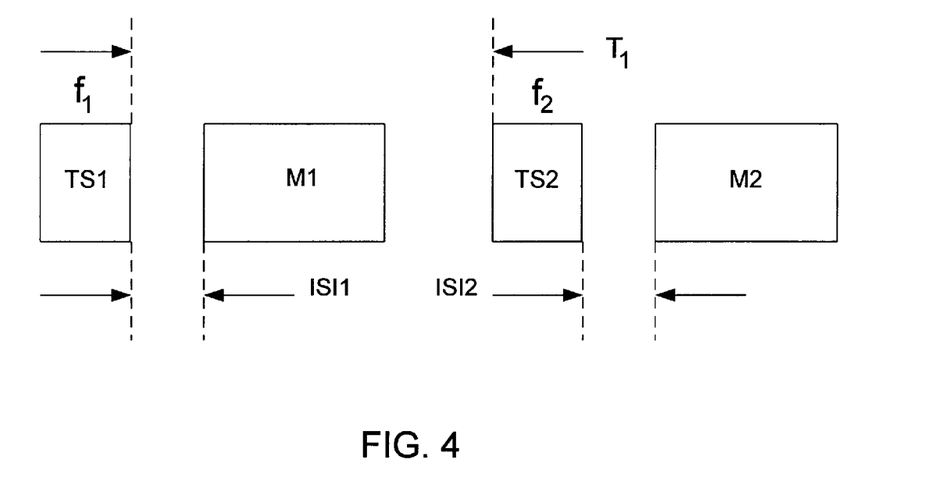
FIG. 4 illustrates, in accordance with one embodiment of the present invention, exemplary tonal stimuli TS1 and TS2, which are administered to the test subject as a sequential pair of tonal stimuli to test for frequency salience.

FIG. 4 illustrates, in accordance with one embodiment of the present invention, exemplary tonal stimuli TS1 and TS2, which are administered to the test subject as a sequential pair of tonal stimuli to test for frequency salience. Each of tonal stimuli TS1 and TS2 preferably has a relatively short duration. In one example, a tone duration of about 20 milliseconds works well for tonal stimulus TS1 and/or tonal stimulus TS2. However, a tone duration may range from between about 10 milliseconds and about 1000 milliseconds.

As shown in FIG. 4, tonal stimulus TS1 is separated from tonal stimulus TS2 by a time T1, which is preferably sufficiently long such that this time value T1 does not become a significant variable in the frequency salience test. A time value of about 800 milliseconds works well in one example. However, this time value T1 may range from between about 0 milliseconds (since the lower limit is bounded by the duration of the masker, which may be 0) and about 2000 milliseconds. To substantially eliminate loudness (amplitude) as a significant variable, tonal stimuli TS1 and TS2 again preferably have the same amplitude. In general, any amplitude within the range of healing comfort may be employed, e.g., about 70 dB SPL in one example.

To eliminate the effect of frequency discrimination, the pair of tonal stimuli of FIG. 4 preferably assume fixed frequency values within the speech frequency range. As such, their frequency separation value is also fixed. Preferably, this frequency separation value is substantially higher than the minimum frequency separation value that people with RD can begin to distinguish the frequencies of different tonal stimuli. In one example, the first tonal stimuli has a frequency of either about 900 Hz or 1100 Hz, with the second tonal stimuli having a frequency of either about 1100 Hz or 900 Hz respectively. In this manner, their frequency separation value is kept relatively high, e.g., about 200 Hz which is substantially higher than the 100 Hz frequency separation threshold at which people with RD begin to have difficulty making frequency discrimination.

Further, each tonal stimulus is followed by a respective masking sound. As shown in FIG. 4, tonal stimulus TS1 is followed by a masking sound M1 after an inter-stimulus interval of ISI1, and tonal stimulus TS2 is followed by a masking sound M2 after an inter-stimulus interval of ISI2. In one example, the masking sound is a bandpass noise having a flat spectrum of over the frequency range of 600–1400 Hz. Note that although FIG. 4 depicts a backward masking situation (i.e., the situation in which the mask follows the sound), a forward or simultaneous masking procedure may be employed if desired.

To test for frequency salience, the inter-stimulus interval ISI1 and/or ISI2 is permitted to progressively reduce in subsequent tonal stimuli pairs. For each tonal stimuli pair, the test subject is asked to listen to the first tonal stimulus, then the first masking sound, then the second tonal stimulus, and then the second masking sound in sequence. These tonal stimuli and masking sounds may be generated by the aforementioned computer system using its software and/or hardware and administered to the test subject via an appropriate transducer such as the speaker or headphone. Thereafter, the test subject is asked to identify which of the two tonal stimuli has the higher frequency. The response may be input into the computer system using the aforementioned input device, e.g., a mouse, keyboard, or the like.

At some inter-stimulus interval (ISI) value, the test subject's answer will become inaccurate. It is believed that the way the frequencies of the tonal stimuli are represented in the mind of those suffering or likely to suffer from RD are less stable than in normal people. Accordingly, those suffering or likely to suffer from RD would have difficulty with the identity of the tonal stimuli, i.e., difficulty with identifying, retaining, and comparing the tonal stimuli in the presence of a closely spaced masking sound.

When this happens, the test may be discontinued or may be permitted to continue for some time with the inter-stimulus interval (ISI) values centered around the point at which frequency salience previously failed in order to eliminate freak errors. As mentioned, an adaptive staircase procedure may be employed wherein the ISI value is progressively reduced until frequency salience failure occurs. After frequency salience failure occurs, the ISI values may be arbitrarily enlarged and then progressively reduced again to validate the failure. This sequence may occur many times if desired.

It has been found that people with RD tend to require a much larger ISI between the tonal stimulus and its respective masking sound for reliable frequency salience responses. By way of example, an ISI of about 100 milliseconds or more may be needed for reliable frequency salience response by people with RD, versus about nearly zero ISI for normal people.

Figure 5:
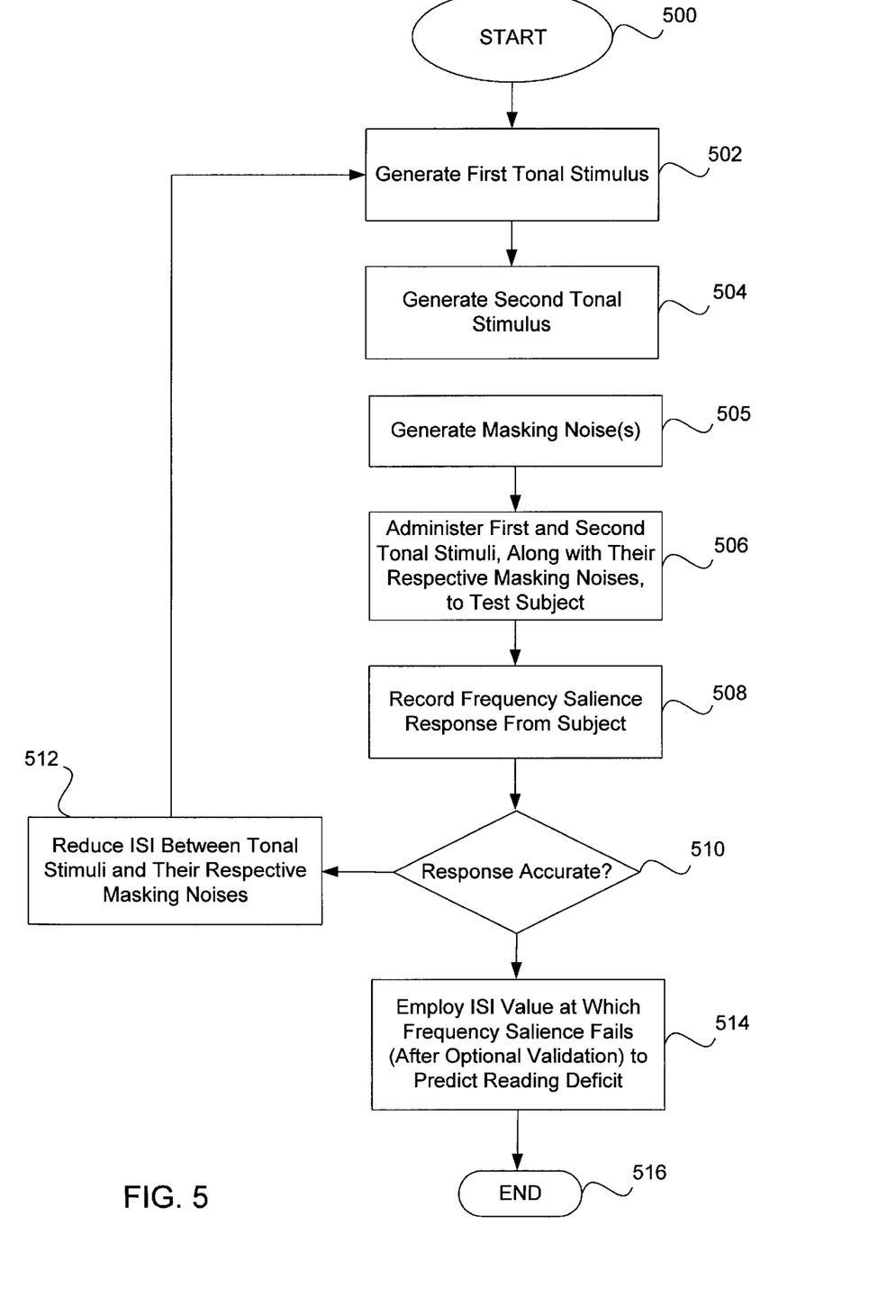
FIG. 5 illustrates, in accordance with one aspect of the present invention, the computer-implemented technique for generating the tonal stimuli employed for RD prediction based on frequency salience.

FIG. 5 illustrates, in accordance with one aspect of the present invention, the computer-implemented technique for generating the tonal stimuli employed for RD prediction based on frequency salience. In step 502, the first tonal stimulus is generated. In step 504, the second tonal stimulus is generated. In step 505, the masking noises are generated. Of course this masking noise generation step may precede any of steps 502 and/or 504 if desired. In step 506, the first and second tonal stimuli, along with their respective masking noises, are administered to the test subject. However, it may be possible, in one embodiment, to administer each tonal stimulus and masking noise after it is generated independent of the other tonal stimulus and/or masking noise. In step 508, the frequency salience response from the test subject is recorded. If the response is accurate (step 510), the ISI value between the tonal stimuli and their respective masking noises are reduced (step 512), and the method returns to step 502 to generate another tonal stimuli pair. On the other hand, if the response is inaccurate (as determined in step 510), the ISI value at which frequency salience fails is employed to predict RD (step 514). As also indicated in step 514, additional validation steps (e.g., the aforementioned adaptive staircase procedure) may be employed to ensure the accuracy of the test.

Repetition Test

Figure 6:
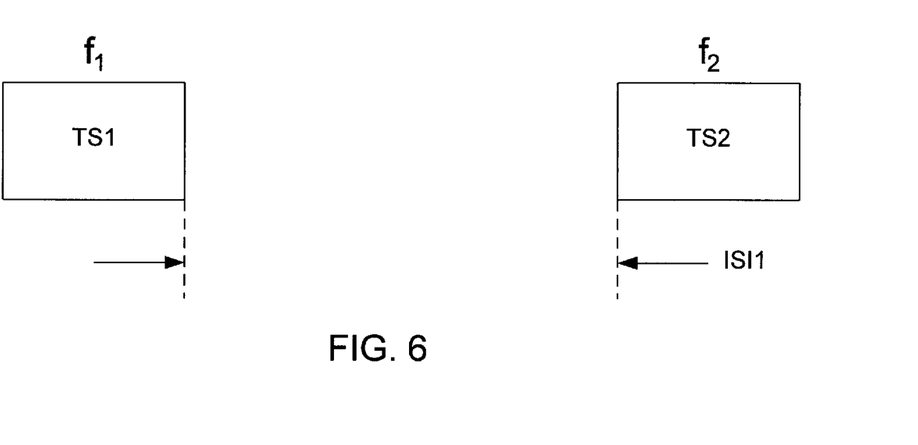
FIG. 6 illustrates, in accordance with one embodiment of the present invention, exemplary tonal stimuli TS1 and TS2, which are administered to the test subject as a sequential pair of tonal stimuli to test for repetition.

FIG. 6 illustrates, in accordance with one embodiment of the present invention, exemplary tonal stimuli TS1 and TS2, which are administered to the test subject as a sequential pair of tonal stimuli to test for repetition. Each of tonal stimuli TS1 and TS2 preferably has a duration between about 10 ms and about 500 ms, preferably between about 20 ms and about 80 ms, and preferably has a duration of about 20 ms.

As shown in FIG. 6, tonal stimulus TS1 is separated from tonal stimulus TS2 by a variable inter-stimulus interval ISI1. As the test progresses, this inter-stimulus interval time ISI1 is progressively reduced. An initial ISI value of about 500 milliseconds or greater works well in one example. To substantially eliminate loudness (amplitude) as a significant variable, tonal stimuli TS1 and TS2 again preferably have the same amplitude. In general, any amplitude within the range of hearing comfort may be employed, e.g., about 70 dB SPL in one example.

To eliminate the effect of frequency discrimination, the pair of tonal stimuli of FIG. 6 may assume fixed frequency values within the speech frequency range. As such, their frequency separation value is also fixed. Preferably, this frequency separation value is substantially higher than the minimum frequency separation value that people with RD can begin to distinguish the frequencies of different tonal stimuli. In one example, the first tonal stimuli has a frequency of either about 800 Hz or 1200 Hz, with the second tonal stimuli also having a frequency of either about 1200 Hz or 800 Hz. In this manner, their frequency separation value is kept relatively high, e.g., about 400 Hz which is substantially higher than the 100 Hz frequency separation threshold at which people with RD begin to have difficulty making frequency discrimination in the one example discussed earlier. Again, the minimum frequency separation value for a test depends, in part, on other parameters of the test, e.g., duration of each tone, amplitude of each tone, ISI, the structure of the test sequence.

To perform the repetition test, the inter-stimulus interval ISI1 is permitted to progressively reduce in subsequent tonal stimuli pairs. For each tonal stimuli pair, the test subject is asked to listen to the first tonal stimulus, then the inter-stimulus interval (ISI), then the second tonal stimulus in sequence. These tonal stimuli and ISI may be generated by the aforementioned computer system using its software and/or hardware and administered to the test subject via an appropriate transducer such as the speaker or headphone. Thereafter, the test subject is asked to identify the two tonal stimuli in the light order. For this test, more complex stimuli than simple tones, e.g., complex tones or natural sounds, may also be employed if desired. The response may be input into the computer system using the aforementioned input device, e.g., a mouse.

At some inter-stimulus interval (ISI) value, the test subject's answer will become inaccurate. When this happens, the test may be discontinued or may be permitted to continue for some time with the inter-stimulus interval (ISI) values centered around the point at which the repetition test subject previously failed in order to eliminate freak errors. As mentioned, an adaptive staircase procedure may be employed wherein the ISI value is progressively reduced until repetition testing failure occurs. After failure occurs, the ISI value may be arbitrarily enlarged and then progressively reduced again to validate the failure. This sequence may occur many times if desired.

It has been found that people with RD tend to require a much larger ISI between the tonal stimuli for reliable identification of the tonal stimuli. The minimum ISI value for a test depends, in part, on other parameters of the test, e.g., duration of each tone, amplitude of each tone, the structure of the test sequence, and the like. In one test, an ISI of about 100 milliseconds or more may be needed for reliable responses by people with RD, versus about nearly zero ISI for normal people. If three separate tonal stimuli are employed (instead of the above-described two), a person suffering from or susceptible to RD would likely need hundreds of milliseconds more ISI than a normal person, which tends to require only about 30–50 milliseconds to reliably identify the tonal stimuli.

Figure 7:
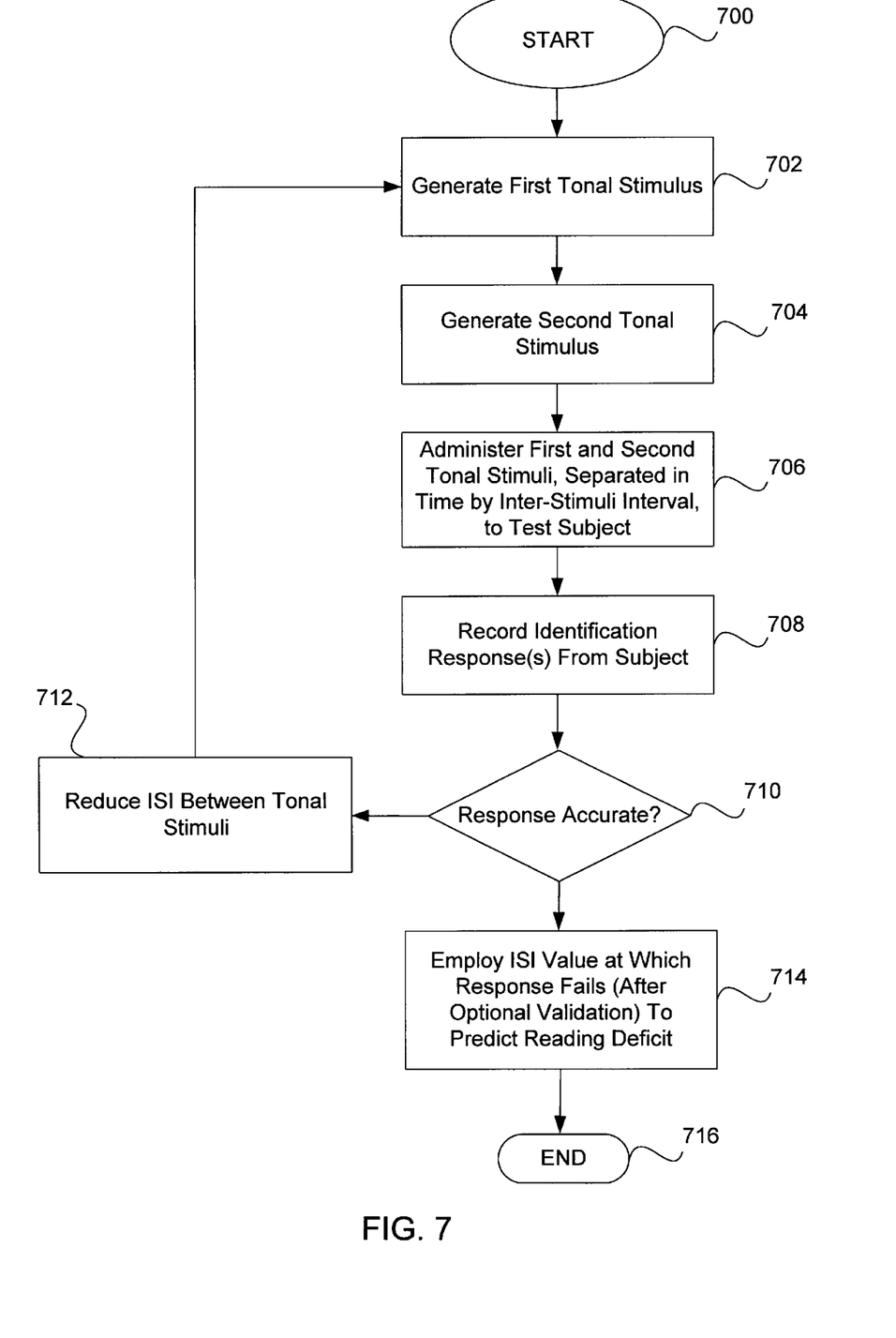
FIG. 7 illustrates, in accordance with one aspect of the present invention, the computer-implemented technique for generating the tonal stimuli employed for RD prediction based on repetition.

FIG. 7 illustrates, in accordance with one aspect of the present invention, the computer-implemented technique for generating the tonal stimuli employed for RD prediction based on repetition. In step 702, the first tonal stimulus is generated. In step 704, the second tonal stimulus is generated. In step 706, the first and second tonal stimuli separated by their initial ISI, are administered to the test subject. However, it may be possible, in one embodiment, to administer each tonal stimulus after it is generated independent of the other tonal stimulus. In step 708, the response film the test subject is recorded. As mentioned earlier, the test subject is asked to identify and report the two stimuli in the order presented.

If the response is accurate (step 710), the ISI value between the tonal stimuli is reduced (step 712), and the method returns to step 702 to generate another tonal stimuli pair. On the other hand, if the response is inaccurate (as determined in step 710), the ISI value at which repetition fails is employed to predict RD (step 714). As also indicated in step 714, additional validation steps (e.g., the aforementioned adaptive staircase procedure) may be employed to ensure the accuracy of the test.

While this invention has been described in terms of several preferred embodiments, there are alterations, permutations, and equivalents which fall within the scope of this invention. By way of example, although the acoustical tests are individually described herein for ease of comprehension, a battery of acoustical tests for the purpose of determining RD may include any combination of the tests described. It is therefore intended that the following appended claims be interpreted as including all such alterations, permutations, and equivalents as fall within the true spirit and scope of the present invention.

What is claimed is:

1. A computer-implemented method for predicting reading deficit in a human being based on acoustic measurements, comprising:
    (a) generating a first tonal stimulus having a first frequency;
    (b) generating a second tonal stimulus having a second frequency;
    (c) providing said first tonal stimulus to said human being;
    (d) providing said second tonal stimulus to said human being;
    (e) receiving a response from said human being, said response having at least two response values, a first response value of said two response values indicating a first perception by said human being that said first tonal stimulus equals said second tonal stimulus, said second response value of said two response values indicating a second perception of said human being that said first tonal stimulus differs from said second tonal stimulus; and
    (f) ascertaining a frequency difference at which said response becomes inaccurate, said frequency difference representing a difference between said first frequency and said second frequency, said frequency difference indicating said human being susceptible to said reading deficit if said frequency difference is above a predefined value.

2. The computer-implemented method of claim 1, further comprising:
    modifying at least one of said first frequency and said second frequency to reduce said frequency difference if said response is accurate, and
    repeating steps (a) through (f).

3. The computer-implemented method of claim 2, further comprising:
    modifying at least one of said first frequency and said second frequency to increase said frequency difference if said response is inaccurate, and
    repeating steps a through f.

4. The computer-implemented method of claim 1, wherein said human being is of a pre-reading age.

5. A computer-implemented method for predicting reading deficit in a human being, comprising:
    (a) generating a set of tonal stimuli, including at least a first tonal stimulus and a second tonal stimulus, said first tonal stimulus being separated from said second tonal stimulus by an interval;
    (b) providing said set of tonal stimuli to said human being;
    (c) receiving a response from said human being, said response from said human being indicating a perception by said human being pertaining to said set of tonal stimuli;
    (d) ascertaining a first parameter pertaining to said set of tonal stimuli at which said response is inaccurate, said first parameter being one of a frequency parameter and a time parameter, said first parameter indicating said human being susceptible to said reading deficit if said first parameter is above a predefined parameter value.

6. The computer-implemented method of claim 5 further comprising:
    modifying one of said first tonal stimulus, said second tonal stimulus, and said interval if said response is accurate; and
    repeating steps (a) through (d).

7. The computer-implemented method of claim 6 wherein said modifying comprises modifying at least one of a first frequency of said first tonal stimulus and a second frequency of said second tonal stimulus to reduce a difference between said first frequency and said second frequency, said first parameter representing said frequency difference and said predefined parameter value representing a predefined frequency value.

8. The computer-implemented method of claim 7 wherein said predefined frequency value is above about 50 Hertz.

9. The computer-implemented method of claim 7 wherein said set of tonal stimuli is independent of whether said human being is fluent in a given language.

10. The computer-implemented method of claim 7 wherein said human being is a pre-reading child.

11. The computer-implemented method of claim 6 wherein said modifying comprises reducing said interval, said first parameter representing said interval and said predefined parameter value representing a predefined time period.

12. The computer-implemented method of claim 11 wherein said predefined time period is about 100 milliseconds.

13. The computer-implemented method of claim 12 wherein said human being is a pre-reading child.

14. The computer-implemented method of claim 5 wherein said set of tonal stimuli is independent of whether said human being is fluent in a given language.

15. The computer-implemented method of claim 5 wherein said human being is a pre-reading child.

16. The computer-implemented method of claim 5 wherein said set of tonal stimuli further including a first masking sound and a second masking sound, said first masking sound being separated from said first tonal stimulus by a first time gap, said second masking sound being separated from said second tonal stimulus by a second time gap, said method further comprising:
    reducing at least one of said first time gap and said second time gap; and
    repeating steps (a) through (d).

* * * * *